(12) United States Patent
Takimoto et al.

(10) Patent No.: US 10,311,559 B2
(45) Date of Patent: Jun. 4, 2019

(54) INFORMATION PROCESSING APPARATUS, INFORMATION PROCESSING METHOD, AND STORAGE MEDIUM

(71) Applicant: CANON KABUSHIKI KAISHA, Tokyo (JP)

(72) Inventors: Masafumi Takimoto, Kawasaki (JP); Yusuke Mitarai, Tokyo (JP); Katsuhiko Mori, Kawasaki (JP); Tomotaka Fujimori, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/528,072

(22) PCT Filed: Dec. 3, 2015

(86) PCT No.: PCT/JP2015/006002
§ 371 (c)(1),
(2) Date: May 18, 2017

(87) PCT Pub. No.: WO2016/092779
PCT Pub. Date: Jun. 16, 2016

(65) Prior Publication Data
US 2017/0323437 A1 Nov. 9, 2017

(30) Foreign Application Priority Data

Dec. 12, 2014 (JP) .................................. 2014-251881
Sep. 24, 2015 (JP) .................................. 2015-187463

(51) Int. Cl.
*G06T 7/00* (2017.01)
*G01N 21/88* (2006.01)
(Continued)

(52) U.S. Cl.
CPC ........ *G06T 7/0002* (2013.01); *G01N 21/8806* (2013.01); *G06F 17/18* (2013.01);
(Continued)

(58) Field of Classification Search
CPC ...... G01N 21/8806; G06F 17/18; G06K 9/00; G06T 1/0007; G06T 7/0002; G06T 2207/20081
See application file for complete search history.

(56) References Cited

U.S. PATENT DOCUMENTS 6,983,065 B1 * 1/2006 Akgul .................. G06K 9/4619
348/125
6,990,364 B2 * 1/2006 Ruchti ............... A61B 5/14532
600/310

(Continued)

FOREIGN PATENT DOCUMENTS

JP      2010102690 A    5/2010
JP      2010175305 A    8/2010

*Primary Examiner* — Mekonen T Bekele
(74) *Attorney, Agent, or Firm* — Canon U.S.A., Inc. IP Division

(57) ABSTRACT

To present a determination result with respect to input data and also a reason of the determination result to a user, an extraction unit configured to extract a plurality of feature amounts from an image including an inspection target object, a determination unit configured to determine an anomaly degree of the inspection target object on the basis of the extracted feature amounts, and an image generation unit configured to generate a defect display image representing a defect included in the inspection target object on the basis of contribution degrees of the respective feature amounts with respect to the determined anomaly degree are provided.

13 Claims, 15 Drawing Sheets

(51) Int. Cl.
  *G06F 17/18* (2006.01)
  *G06T 1/00* (2006.01)
  *G06K 9/42* (2006.01)
  *G06K 9/46* (2006.01)
  *G06K 9/62* (2006.01)

(52) U.S. Cl.
  CPC .............. *G06K 9/42* (2013.01); *G06K 9/4614* (2013.01); *G06K 9/6284* (2013.01); *G06T 1/0007* (2013.01); *G06T 2207/20081* (2013.01)

(56) References Cited

U.S. PATENT DOCUMENTS

| | | | |
|---|---|---|---|
| 7,369,686 B2* | 5/2008 | Yokono | G06K 9/00221 |
| | | | 382/118 |
| 8,824,805 B2* | 9/2014 | Kim | G06Q 10/00 |
| | | | 382/195 |
| 9,672,439 B2* | 6/2017 | Yamanaka | G06K 9/4671 |
| 9,959,482 B2* | 5/2018 | Uemura | G06K 9/4614 |
| 2005/0185835 A1* | 8/2005 | Matsugu | G06K 9/4619 |
| | | | 382/159 |
| 2006/0192117 A1* | 8/2006 | Miyai | H01J 37/265 |
| | | | 250/310 |
| 2008/0137917 A1* | 6/2008 | Okubo | G06K 9/00268 |
| | | | 382/118 |
| 2009/0116734 A1* | 5/2009 | Willis | G06K 9/6256 |
| | | | 382/159 |
| 2010/0239154 A1 | 9/2010 | Fujimori | |
| 2015/0294181 A1* | 10/2015 | Yamanaka | G06K 9/4671 |
| | | | 382/203 |
| 2015/0379357 A1* | 12/2015 | Datta | G06K 9/00771 |
| | | | 382/155 |
| 2016/0155026 A1* | 6/2016 | Hashiguchi | G06K 9/6267 |
| | | | 382/159 |
| 2016/0217338 A1* | 7/2016 | Li | G06K 9/00765 |
| 2018/0053296 A1* | 2/2018 | Hattori | G01N 33/4833 |

* cited by examiner

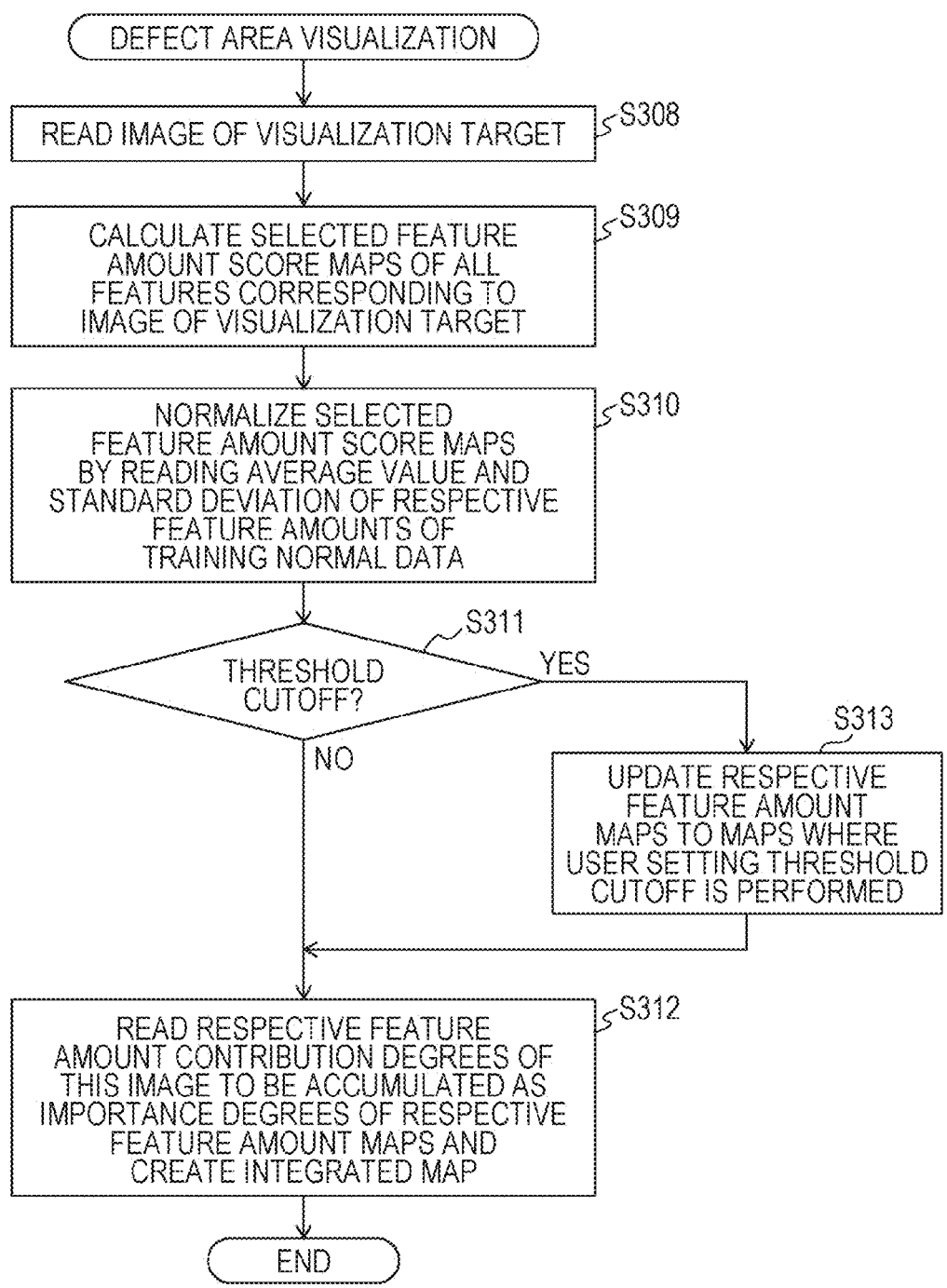

INFORMATION PROCESSING APPARATUS, INFORMATION PROCESSING METHOD, AND STORAGE MEDIUM

TECHNICAL FIELD

The present invention relates to a method of picking up an image of an object and determining whether the object is normal or abnormal on the basis of the picked-up image.

BACKGROUND ART

A device has been proposed in which, when a signal such as an image is input, and an attribute or the like of the input signal is discriminated by a discriminator, a reason of a discrimination result is visualized and presented to a user. For example, in the field of an automatic appearance inspection, when a determination is made as to whether an inspection target is normal or abnormal by using an image including an inspection target, if a result of the determination that the inspection target is abnormal and also the a reason for the above-described determination can be provided, this information is useful to the user. That is, when an area corresponding to a cause of the anomaly can be visualized as an image, the user can intuitively find out a determination reference of an automatic appearance inspection apparatus. Accordingly, the above-described configuration is useful when a parameter related to the inspection is adjusted and when the number of occurrences of the particular abnormal patterns is found out to provide a feedback to a process in a production line as a countermeasure to carry out a modification.

For example, PTL 1 discloses that one determination image is created from a plurality of images obtained by shooting the inspection target object under a plurality of illumination conditions, and the normal/abnormal inspection is performed by using the determination image. With regard to the determination image created by the method according to PTL 1, in a case where the inspection target object is determined as abnormal, an area where an anomaly exists is distinguished from the other normal area to be visualized, and a user can easily understand which area is abnormal.

However, the creation of the determination image according to PTL 1 is optimized in accordance with previously set desired inspection items, and it is difficult to cope with a complicated inspection or an unidentified defect.

In view of the above, PTL 2 discloses a method of extracting a previously selected feature amount from an input image and determining whether it is normal or abnormal by using the feature amount without generating the determination image as in PTL 1. According to this method, by previously learning a feature amount that affects the normal or abnormal discrimination without generating the determination image, it is possible to accurately determine whether it is normal or abnormal.

However, even when the method of outputting the inspection result without creating the determination image as in PTL 2 is employed, an analysis on the result may also be desired to be carried out in some cases. That is, although a normal/abnormal discrimination accuracy is extremely important in the appearance inspection of parts, finding out an anomaly cause corresponding to additional information (a type of the anomaly, a location, or the like) and easily grasping a tendency may also be useful information to the user in many cases. According to the method disclosed in PTL 2, a problem occurs that the anomaly cause is not presented to the user.

CITATION LIST

Patent Literature

PTL 1: Japanese Patent Laid-Open No. 2010-175305
PTL 2: Japanese Patent Laid-Open No. 2010-102690

SUMMARY OF INVENTION

To address the above-described problem, a non-defective product inspection apparatus according to an aspect of the present specification includes, for example, an extraction unit configured to extract a plurality of feature amounts from an image including an inspection target object, a determination unit configured to determine an anomaly degree of the inspection target object on the basis of the extracted feature amounts, and an image generation unit configured to generate a defect display image representing a defect included in the inspection target object on the basis of contribution degrees of the respective feature amounts with respect to the anomaly degree determined by the determination unit.

In addition, an information processing apparatus according to an aspect of the present specification includes, for example, an extraction unit configured to extract a plurality of feature amounts from a plurality of images including an inspection target object, a determination unit configured to determine an anomaly degree of the inspection target object on the basis of the extracted feature amounts, and an image generation unit configured to generate an image in which a defect included in the inspection target object is emphasized and displayed, by synthesizing the plurality of images to one another on the basis of contribution degrees of the respective feature amounts with respect to the anomaly degree determined by the determination unit.

According to the present specification, it is possible to present the determination result with respect to the input data and also the reason of the determination result to the user.

Further features of the present invention will become apparent from the following description of embodiments with reference to the attached drawings.

BRIEF DESCRIPTION OF DRAWINGS

FIG. 4 is a processing flow chart according to the first embodiment.

DESCRIPTION OF EMBODIMENTS

Hereinafter, with respect to the drawings, embodiments (exemplary embodiments) of the present invention will be described.

Before the respective embodiments of the present invention will be described, a hardware configuration to which an information processing apparatus 101 according to the respective embodiments is mounted will be described with respect to FIG. 1.

Figure 1:
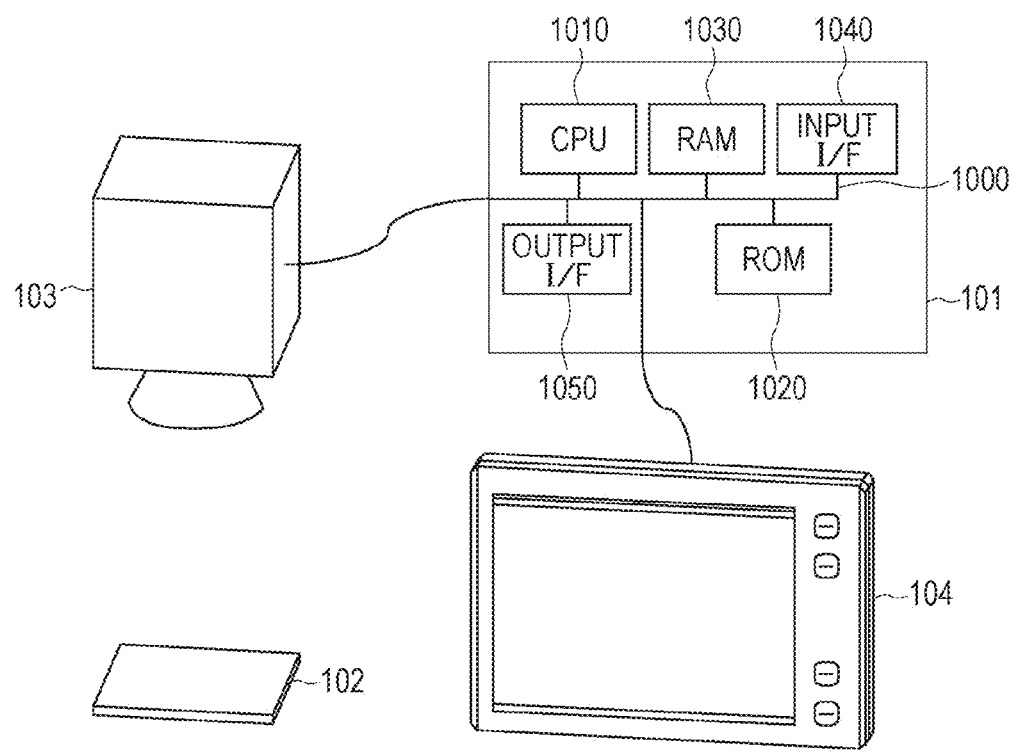
FIG. 1 illustrates a configuration example of an inspection system using an information processing apparatus according to a first embodiment.

In FIG. 1, a CPU 1010 controls the respective devices connected via a bus 1000 in an overall manner. The CPU 1010 reads out process steps and programs stored in a read-only memory (ROM) 1020. Respective process programs, device drivers, and the like including an operating system (OS) according to the present embodiment are stored in the ROM 1020 and temporarily stored in a random access memory (RAM) 1030 to be appropriately executed by the CPU 1010. An input signal is input to an input interface (I/F) 1040 from an external apparatus (such as a display apparatus or an operation apparatus) in such a format that the signal can be processed by the information processing apparatus 101. An output signal is output from an output I/F 1050 to the external apparatus (display apparatus) in such a format that the signal can be processed by the display apparatus.

First Embodiment

Hereinafter, a first embodiment of the present invention will be described with respect to the drawings.

FIG. 1 is a conceptual diagram of an appearance inspection system using the information processing apparatus 101 according to the present embodiment.

An image pickup apparatus 103 is constituted by a video camera or the like that can obtain a picture (image pattern) of a surface of an inspection target object 102 and transmits the obtained video to the information processing apparatus 101. The information processing apparatus 101 performs information processing for an appearance inspection by using the transmitted video picture.

The inspection target object 102 is an object as a target to be determined as a non-defective product or a defective product by the information processing apparatus 101. Examples of the inspection target object 102 include a rubber formed product used for an industrial product, a metallic part, a glass formed product such as a lens, a plastic formed product, and the like. Irregularities that are not seen on the non-defective product or unevenness or scratches in processing process may be caused on a surface of the inspection target object 102 in some cases. These defects are detected by the appearance inspection, and the object is detected as the defective product.

Figure 2:
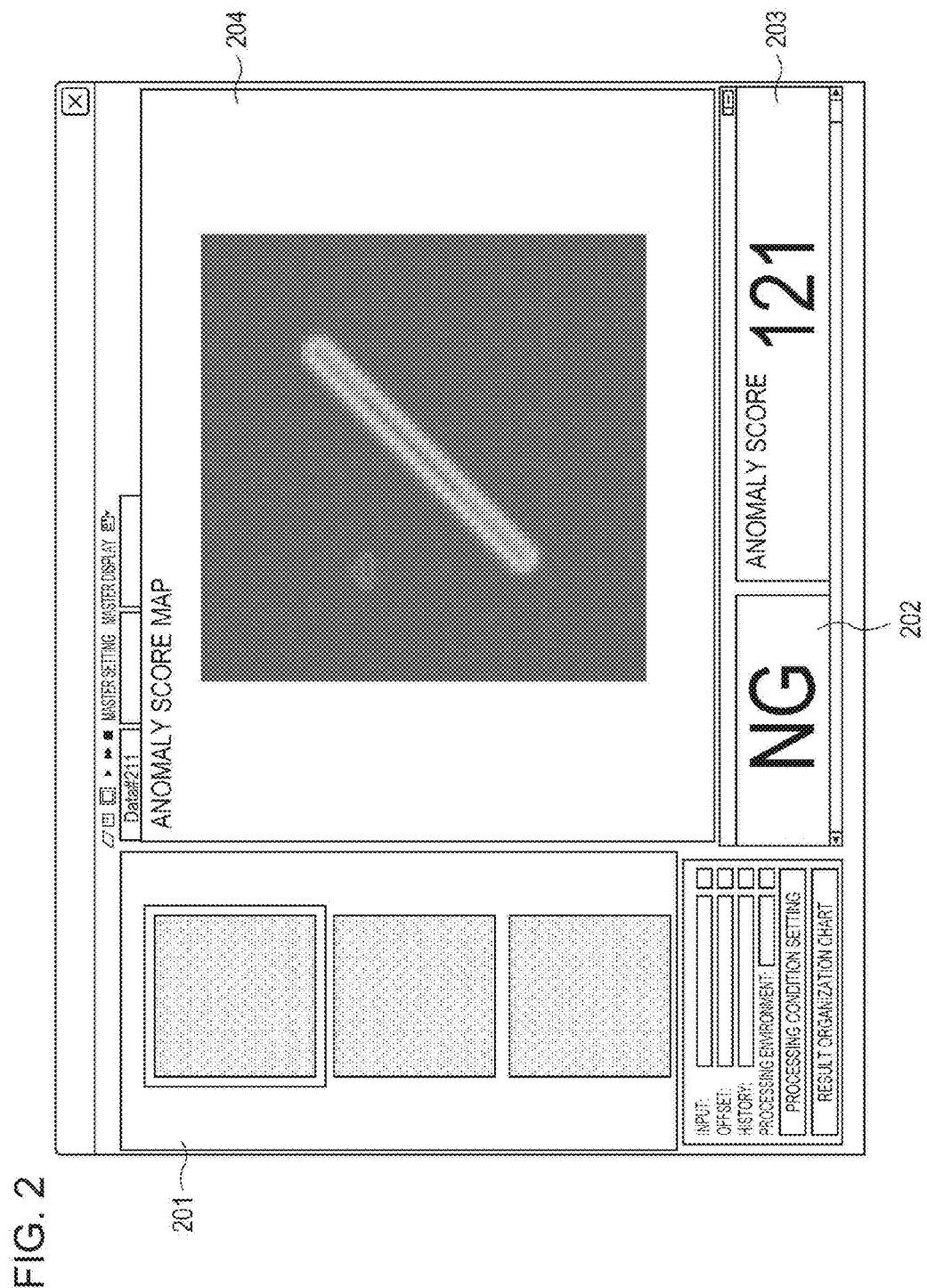
FIG. 2 illustrates a display example of a display apparatus according to the first embodiment.

A display apparatus 104 is constituted by a monitor or the like. FIG. 2 illustrates a display example of a determination result to the display apparatus 104. Images are displayed on an area 201. A normal/abnormal classification result corresponding to an image selected on the area 201 is displayed while being emphasized by a bold frame, and OK/NG is displayed on an area 202. An anomaly score by the discriminator at that time is displayed on an area 203. An anomaly score map with respect to the selected image is displayed on an area 204, which represents a situation where a large scratch-like anomaly, which is difficult to be visually recognized with the image alone, can be easily visually recognized on the anomaly score map displayed on the area 204. That is, while the user checks the image displayed on the area 204, the user can easily understand why the image selected on the area 201 is determined as abnormal.

Figure 5A:
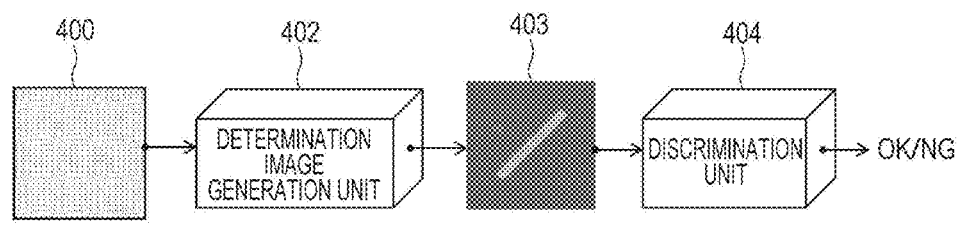
FIG. 5A is a functional block diagram of a related-art apparatus.
Figure 5B:
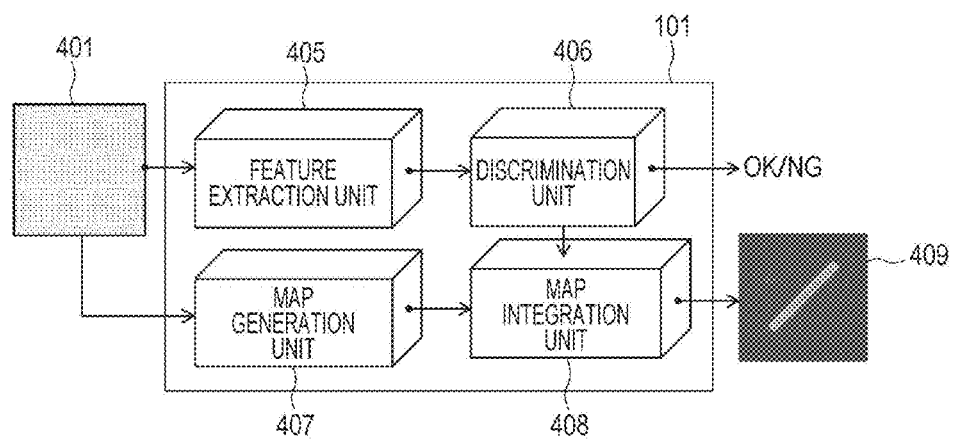
FIG. 5B is a functional block diagram of the information processing apparatus according to the first embodiment.

FIG. 5A is a functional block of a related-art apparatus that generates a determination image for the visualization from an input image 400 as described in PTL 1. FIG. 5B is a functional block of the present embodiment. In FIG. 5A, a discrimination of the input image 400 is performed in a manner that a determination image generation unit 402 is generated in a determination intermediate image 403, and a discrimination unit 404 performs a discrimination as to whether the input image 400 is normal or abnormal on the basis of a result of the determination intermediate image 403. Hereinafter, respective functions constituting the information processing apparatus according to the present embodiment in FIG. 5B will be described.

An input image 401 is an image of an inspection target object picked up by an image pickup unit.

A feature extraction unit 405 extracts feature amounts from the input image 401. According to the present embodiment, a maximum value, an average value, a variance, a kurtosis, a skewness, a contrast, a maximum gradient, or the like is extracted as feature amounts from an image obtained through a conversion of an input image. Specific processing will be described below.

A discrimination unit 406 determines whether the inspection target object included in the input image 401 is normal or abnormal by using the feature amounts extracted by the feature extraction unit 405.

A map generation unit 407 generates maps of the respective feature amounts corresponding to the extracted features from the input image 401. The maps according to the present embodiment have a two-dimensional array having the same number of dimensions as the input image, and scores are stored in the respective elements. The map is not limited to this format of course.

A map integration unit 408 refers to contribution degrees of the respective feature amounts with respect to the discrimination result obtained at the time of the discrimination by the discrimination unit 406 and integrates the plurality of maps generated by the map generation unit 407 for the respective feature amounts to one another to generate a visualized image 409 in which a defect candidate area is visualized. The map integration unit 408 outputs the generated visualized image 409.

The above-described respective functional units are realized while the CPU 1010 extends a program stored in the ROM 1020 onto a RAM 1030 and executes processings following respective flow charts that will be described below. For example, in a case where hardware is constructed as a substitute of the software processing using the CPU 1010, a computation unit or a circuit corresponding to the processing of each functional unit described herein may be constructed.

Figure 3:
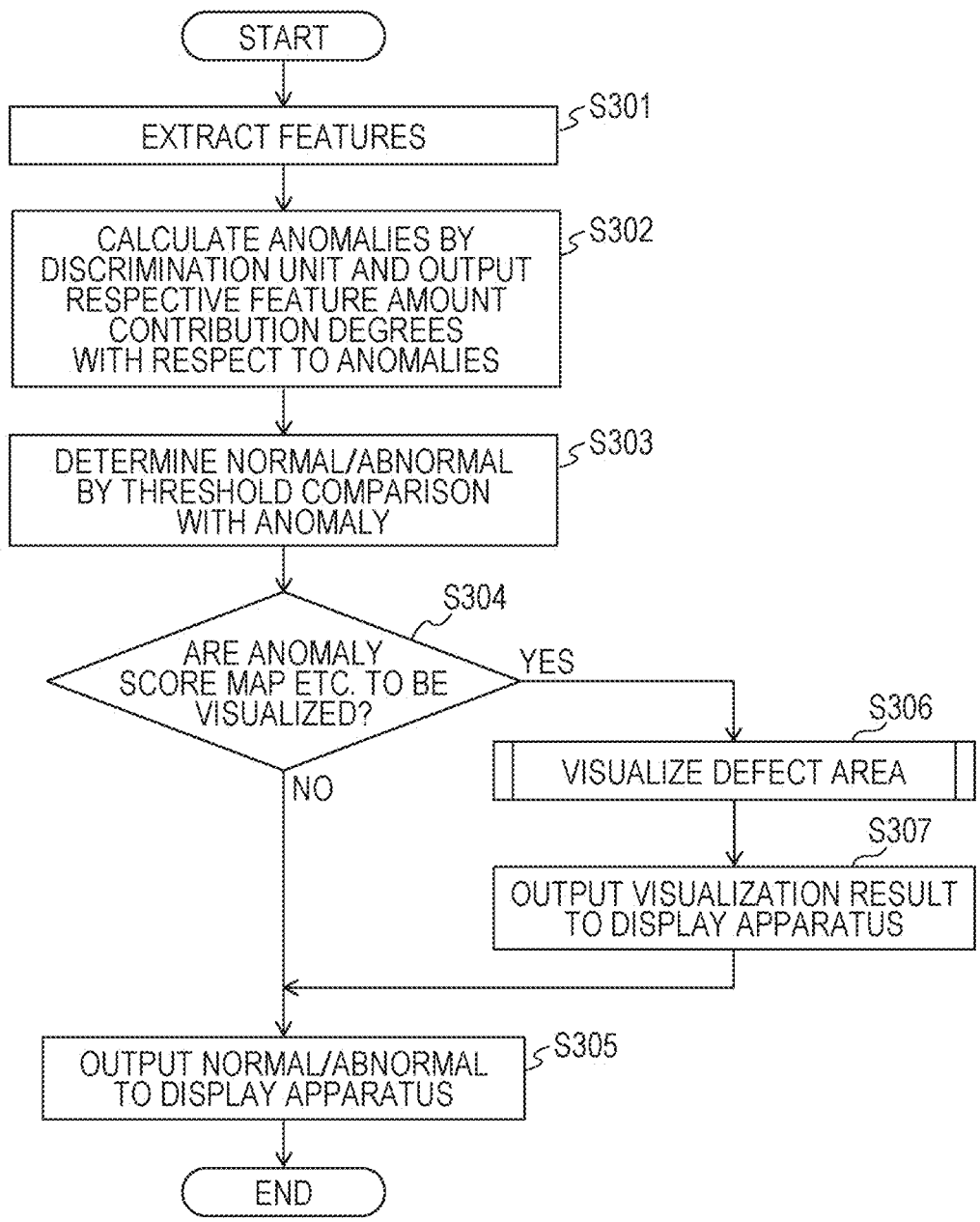
FIG. 3 is a processing flow chart according to the first embodiment.

Hereinafter, the processing flow chart according to the present embodiment will be described with reference to FIG. 3.

Step S301

In step S301, the feature extraction unit 405 extracts N pieces of features from the input image 401 corresponding to the image of the inspection target. Hereinafter, how to determine the feature amounts extracted from the image according to the present embodiment will be described below.

First, the input image 401 is decomposed from high frequency components into frequency component images in vertical, horizontal, and diagonal directions of low frequency components by the filter processing based on Haar Wavelet conversion to generate a plurality of hierarchical images. Then, a plurality of feature amounts are extracted from the plurality of generated hierarchical images. The processing based on the Haar Wavelet conversion is performed on the input image 401 by using filters represented by the following four types of matrices (Expressions 1-A to 1-D).

[Math. 1]

$$\begin{bmatrix} 1 & 1 \\ -1 & -1 \end{bmatrix} \quad \text{(Expression 1-A)}$$

$$\begin{bmatrix} 1 & -1 \\ 1 & -1 \end{bmatrix} \quad \text{(Expression 1-B)}$$

$$\begin{bmatrix} 1 & -1 \\ -1 & 1 \end{bmatrix} \quad \text{(Expression 1-C)}$$

$$\begin{bmatrix} 1 & 1 \\ 1 & 1 \end{bmatrix} \quad \text{(Expression 1-D)}$$

Expression 1-A represents a vertical direction high frequency component filter, Expression 1-B represents a horizontal direction high frequency component filter, Expression 1-C represents a diagonal direction high frequency component filter, and Expression 1-D represents a low frequency component filter. New images are generated which store pixel values corresponding to the images decomposed in terms of the frequency components newly obtained by performing an inner product calculation on 2×2 pixels in the input image 401 by using the filters represented by Expressions 1-A to 1-D. This filter processing is moved over the entire area in the input image 401 without overlapping of the 2×2 areas, and images are obtained in which image sizes of four types of a vertical direction high frequency component image, a horizontal direction high frequency component image, a diagonal direction high frequency component image, and a low frequency component image are halved lengthwise and crosswise.

Thereafter, the filter processing is further performed on the low frequency component image similarly as in the input image to obtain four types of images including the vertical direction high frequency component image, the horizontal direction high frequency component image, the diagonal direction high frequency component image, and the low frequency component image in the next hierarchical level.

The generation of the images having the image size halved lengthwise and crosswise is repeatedly performed by repeating the above-described processing for decomposing the signal for each frequency and is ended until the repetition is performed up to the hierarchical level at which the decomposition is eventually no longer available. It should be noted that up to how many hierarchical levels the decomposition is performed depends on the size of the input image 401. For example, in the case of decomposition into 8 hierarchical levels, since four images per hierarchical level are obtained, 8×4=32 types of images are obtained (hierarchical image generation).

Next, a plurality of statistical feature amounts are extracted from the 32 types of images. A value such as the maximum value, the average value, the variance, the kurtosis, the skewness, the contrast, or the maximum gradient of the pixel values in each frequency component image (in the hierarchical image) is set as the feature amount extracted herein. Herein, when the number of feature amounts extracted from each of the frequency component images is set as 20, the number of the feature amounts extracted from the single original image is eventually 32×20=640. However, the number of dimensions of the information dealt with in the discrimination processing using all of the feature amounts as many as 640 is high, and a generalizing capability is decreased in many cases by a phenomenon generally called "the curse of dimensionality". In view of the above, a combination of feature amounts appropriate to the discrimination processing is selected in advance by a mechanical leaning method of searching for a feature amount set with which normality and anomaly are accurately distinguished, and it is possible to realize the highly accurate discrimination processing in the actual inspection. Various methods are proposed as a feature selection method of searching for a satisfactory feature amount combination, and numerous techniques including LASSO, graph cut, a feature selection technique using a genetic algorithm, and the like are exemplified. Hereinafter, the number of feature amounts eventually selected in advance by the feature selection processing is set as N (approximately several tens of feature amounts). It should be noted that any discriminator may be used, and a subspace method is used according to the present embodiment. In addition, according to the present embodiment, the Haar Wavelet conversion is used, but the present invention is not limited to this, and a predetermined conversion with which it is possible to generate a plurality of images from the input image 401 may be used.

Step S302

Figure 7:
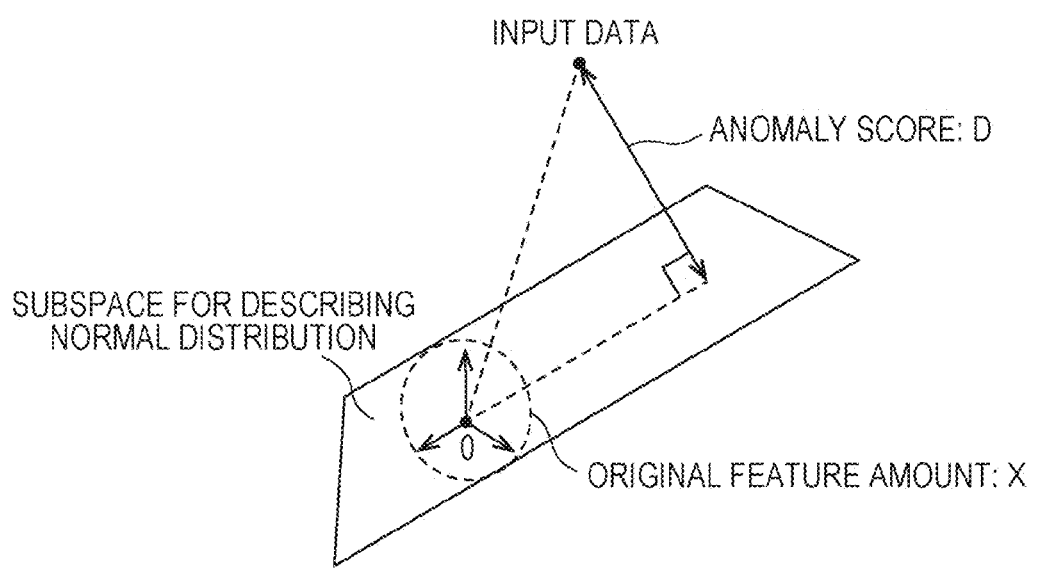
FIG. 7 is an explanatory diagram for describing a case of determining importance degrees of respective feature amounts in an anomaly score according to the first and second embodiments.

In step S302, the discrimination unit 406 obtains the N feature amounts extracted in step S301 and determines whether an anomaly exists on the basis of a distance from a higher dimension surface representing a normal area that has been learnt as a normal distribution by the subspace method. A anomaly score is defined as a numeric conversion of the distance or the like from the normal distribution by the discriminator. According to the present embodiment, the subspace method is used as the discrimination method by the discrimination unit 406. When the input entire feature amounts as illustrated in FIG. 7 is set as X, a hyperplane having an orientation having a maximum pattern distribution variance is learnt by training normal data at the time of the previous learning. A distance D in a direction component orthogonal to the hyperplane from data newly input at the time of testing is used as the distance from the normal distribution, that is, the anomaly score. Thus, an intermediate image for the inspection does not exist, and the normal/abnormal discrimination can be carried out. The distance D can be obtained by subjecting a distribution in a normal feature space desired to be represented by a mean vector Mc (c=1, 2, . . . , C) of the normal data and a hyperplane constituent vector ϕcl (l=1, 2, . . . , L) to an approximate representation by the hyperplane. For the above-described "l", an appropriate dimension number L may be determined, and the L-dimensional hyperplane may be set in the following description.

In the appearance inspection, c denotes the number of classes in a normal state. For example, the inspection in a state in which two normal states are mixed with each other may be executed by setting c=2. For the distance D in the case of c=2, two distances defined by the two normal classes (c=1 and c=2) are calculated, and it is possible to determine as normal when one of the two distances is shorter than or equal to a distance previously set as a threshold. It should be however noted that, since a probability is extremely low that the inspection of two types of parts is performed at the same time by a single inspection process in the appearance inspection in which a precision is demanded in general, c=1 is set hereinafter. In addition, the number of pieces of normal data is set as t. At this time, Mc is represented by Expression 2.

[Math. 2]

$$M_c = \frac{1}{t} \sum_{i=1}^{t} X_{ci} \qquad \text{(Expression 2)}$$

A variance-covariance matrix Σc can be represented by using a feature vector Xci. The variance-covariance matrix Σc is represented by Expression 3.

[Math. 3]

$$\sum_c = \frac{1}{t-1} \sum_{i=1}^{t} (X_{ci} - M_c)(X_{ci} - M_c)^T \qquad \text{(Expression 3)}$$

To define an approximate hyperplane, by using Σc obtained in Expression 3, an eigenvalue problem represented by Expression 4 is solved.

[Math. 4]

$$\sum_c \phi_{cl} = \lambda_{cl} \phi_{cl} \text{ subject to } (\phi_{cl}, \phi_{cr}) = \begin{cases} 1 & (\text{when } l = l') \\ 0 & (\text{when } l = l') \end{cases} \qquad \text{(Expression 4)}$$

Thereafter, while first eigenvalue and eigenvector of Σc are respectively set as λcl and ϕcl, the hyperplane that passes through Mc in Expression 2 by ϕcl corresponding to selected L pieces of larger parts of λcl is defined as a plane for describing the normal distribution. In a case where a feature vector X' extracted from a test sample is an N-dimensional feature vector, the distance D corresponding to the anomaly score is represented by Expression 5 while a j-th element (N is higher than or equal to j, and j is higher than or equal to 1) is set as xj, and similarly, a j-th dimensional element of the mean vector Mc is set as mjc.

[Math. 5]

$$D = \sum_{j=1}^{N} (x_j - m_{jc})^2 - \sum_{l=1}^{L} \{\phi_{cl}^T (X' - M_c)\}^2 \qquad \text{(Expression 5)}$$

Furthermore, together with the calculation of the anomaly score D (the distance D) herein, contribution degrees of the N feature amounts with respect to the anomaly score D are output. The contribution degree mentioned herein refers to a rate of the contribution of each of the feature amounts with respect to the anomaly score D and is used by being read in step S312 when the anomaly score maps are visualized in a later stage. A contribution degree calculation method can be used for the following calculation. When an element in a j-th dimension of a weight W with respect to X' is set as wj, and an eigenvector is set as e, a relationship with the anomaly score D can be represented by Expression 6.

[Math. 6]

$$\begin{aligned} D &= \sum_{j=1}^{N} (x_j - m_{jc})^2 - \sum_{j=1}^{N} e_j^2 (x_j - m_{jc})^2 \qquad \text{(Expression 6)} \\ &= \sum_{j=1}^{N} (1 - e_j^2) x_j^2 - 2(1 - e_j^2) m_{jc} x_j + \sum_{j=1}^{N} (1 - e_j^2) m_{jc}^2 \\ &= \sum_{j=1}^{N} (1 - e_j^2) x_j^2 - 2(1 - e_j^2) m_{jc} x_j + \text{Const.} \end{aligned}$$

Accordingly, the contribution degree wj of the j-th dimensional feature amount to be obtained is calculated as Expression 7.

[Math. 7]

$$w_j = \frac{(x_j - m_{jc}) - e_j^2 (x_j - m_{jc})}{\sum_{j=1}^{N} (x_j - m_{jc}) - e_j^2 (x_j - m_{jc})} \qquad \text{(Expression 7)}$$

The thus calculated wj is output to be used in the visualization process in step S306. In addition, a threshold is previously set with respect to the anomaly score D, and in step S303, the discrimination unit determines as normal or abnormal.

Step S304

In step S304, it is determined as to whether or not defect candidate area visualization based on the anomaly score maps is performed. The user may previously set whether or not the defect candidate area visualization is performed. When it is set that the anomaly score map visualization is not performed, the processing proceeds to step S305. When it is set that the anomaly score map visualization is performed, the processing proceeds to step S306 to perform the defect candidate area visualization. Whether the processing proceeds to step S306 or step S305 may be determined on the basis of the normal or abnormal determination result obtained in step S304. That is, when it is determined as abnormal, the processing may automatically proceed to step S306.

Step S305

In step S305, the map integration unit 408 outputs information as to whether it is normal or abnormal, the anomaly score, and the like to the display apparatus 104.

Step S306

In step S306, the defect area is visualized. This processing will be described by using the processing flow chart of FIG. 4.

Step S308

In step S308, the map generation unit 407 obtains the input image 401.

Step S309

In step S309, the map generation unit 407 calculates score maps representing the scores of the feature amounts extracted in step S301. For example, when one of the N feature amounts extracted in step S301 is the maximum value of the hierarchical images obtained by the Haar Wavelet conversion, the map generated by the map generation unit 407 is the same as the hierarchical image for extracting the maximum value in step S301. In addition, when one of the N feature amounts extracted in step S301 is the average value of the hierarchical images obtained by the Haar Wavelet conversion, images obtained by dividing the hierarchical image into grids having an arbitrary size and calculating the average values in the respective grids are set as score maps.

Step S310

In step S310, the map generation unit 407 performs normalization of the score maps obtained in step S309. A plurality of training images including the non-defective inspection target object are previously converted into score maps corresponding to the respective features by a method similar to step S309, and an average value and a standard deviation of the obtained score maps are calculated to be held, for example, in the ROM 1020. Thereafter, the held average value and standard deviation are read out, and the score maps obtained in step S309 are normalized by using the read values.

Step S311

In step S311, the map integration unit 408 determines whether only values of the score maps higher than or equal to the threshold are left or all the values are left on the basis of the user setting. If the threshold cutoff is set, all the areas lower than or equal to the threshold are set as 0 in step S313.

Step S312

In step S312, the map integration unit 408 reads the contribution degrees of the feature amounts output in step S302 and integrates the respective score maps to one another by using the contribution degrees as importance degrees of the respective score maps to create a defect display image. The process of creating the image on which the importance degrees are affected at this time will be illustrated in a conceptual diagram of FIG. 6. The conceptual diagram of FIG. 6 represents a detail of the map integration unit 408 of FIG. 5B.

Figure 6:
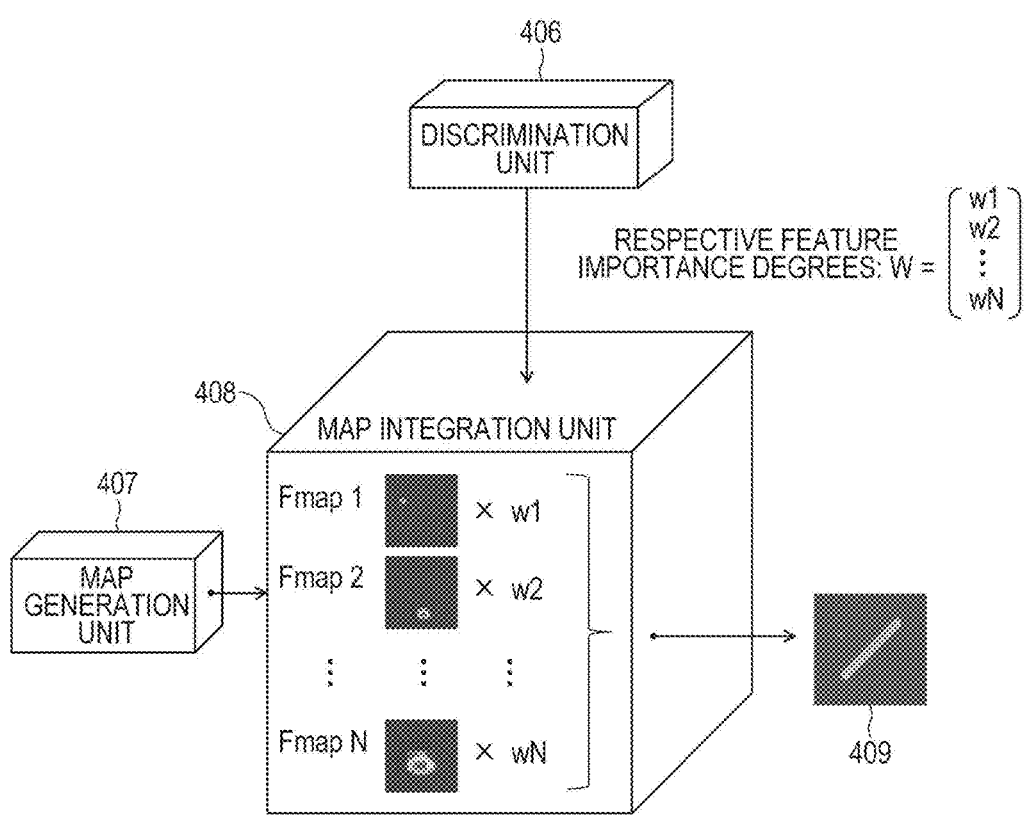
FIG. 6 is a block diagram illustrating a detail of a processing content of a map integration unit of FIG. 5B according to the first embodiment.

The importance degree W calculated in Expression 7 holds respective weights w1 to wN with respect to the input N feature amounts as illustrated in FIG. 6, and these weights are transmitted from the discrimination unit 406 to the map integration unit 408. Then, the respective maps calculated from the N feature amounts are respectively transmitted as Fmap1 to FmapN from the map generation unit 407. Thereafter, the respectively corresponding maps are multiplied by the importance degrees, and a linear sum is calculated for each of the same pixels in all the maps to generate a single defect display image. It should be noted that, when the respective score maps are integrated to one another, the respective score maps are once converted to have the same resolution as that of the original input image 401 and then integrated to one another. The defect display image is an image in which the defect area is emphasized and an image indicating a reason why it is determined as abnormal by the discrimination unit 406.

Step S313

In step S313, the map integration unit 408 sets all scores of the areas having the scores lower than or equal to the threshold as 0 in the respective maps normalized in step S310. Accordingly, since only the defect area has a score, in a case where the defect area is superposed on the input image 401 to be displayed, it is facilitated for the user to recognize the location of the defect area.

Step S307

In step S307, the map integration unit 408 outputs the score maps generated in step S306 to the display apparatus 104 to be displayed. In step S305, the map integration unit 408 outputs the information as to whether it is normal or abnormal, the anomaly score, and the like, and the processing is ended.

According to the present embodiment, the user can intuitively find out the reason why the inspection target is determined as abnormal together with the result of the abnormal determination. For this reason, the above-described configuration is beneficial when the parameter related to the inspection is adjusted and when the number of occurrences of the particular abnormal patterns is found out to provide the feedback to the process in the production line as the countermeasure to carry out the modification.

Second Embodiment

Hereinafter, a second embodiment (exemplary embodiment) of the present invention will be described with respect to the drawings. According to the second embodiment, in a case where a plurality of images are obtained by shooting a single inspection target and a feature amount is extracted from each of the images to perform the appearance inspection, an image indicating a reason of an inspection result is generated.

Figure 8:
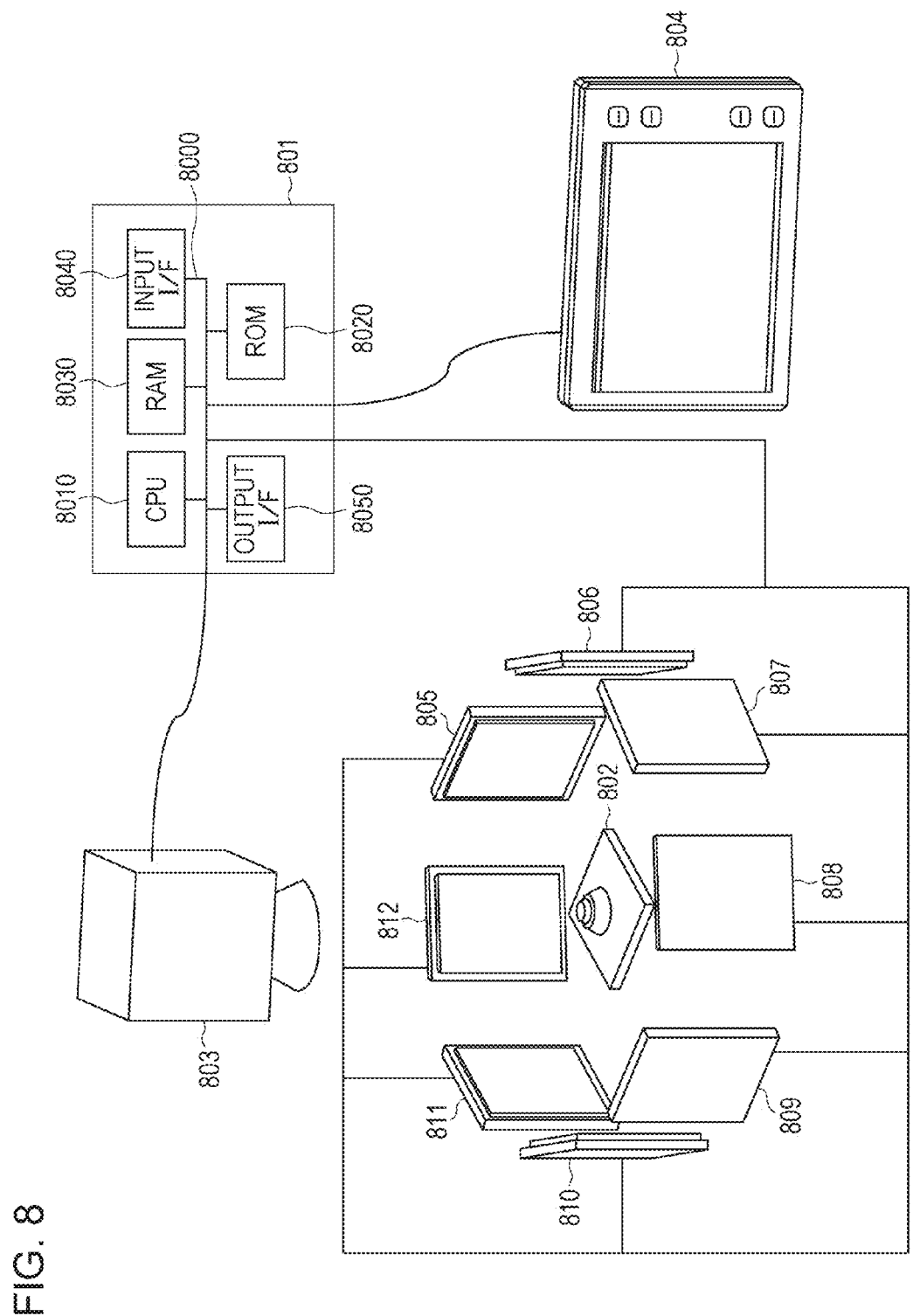
FIG. 8 illustrates a configuration example of the inspection system using the information processing apparatus according to the second and third embodiments.

A hardware configuration to which an information processing apparatus 801 according to the present embodiment is mounted will be described with reference to FIG. 8. The configuration of FIG. 8 is similar to the configuration of FIG. 1 but is designed such that a large irregularity structure is formed on the inspection target 802, and a texture anomaly on irregularities is accurately detected. Thus, a difference resides in that eight illumination apparatuses 805 to 812 are provided, and the illumination apparatuses 805 to 812 are controlled by the information processing apparatus 801 as compared with FIG. 1.

FIG. 8 is a conceptual diagram of the appearance inspection system using the information processing apparatus 801 according to the present embodiment.

An image pickup apparatus 803 is constituted by a video camera or the like that can obtain a picture (image pattern) of a surface of the inspection target 802 and transmits the obtained picture to the information processing apparatus 801. Herein, illumination times of the illumination apparatuses 805 to 812 are controlled in synchronous with the image pickup of the image pickup apparatus 803, and a plurality of types of images related to the inspection target 802 are shot. In FIG. 8, the illumination apparatuses 805 to 812 are exemplified as illuminations having different irradiation angles, but these illumination apparatuses may emit not only visible light or a uniform illumination but also infrared rays or an arbitrary pattern illumination. In particular, in a case where a three-dimensional structure of the inspection target 802 is obtained and used, a plurality of pattern illuminations are emitted to carry out the image pickup. Furthermore, the shooting may be performed under illumination conditions based on combinations of these eight illuminations. According to the present embodiment, descriptions will be given while the image pickup is performed once each under the single illumination condition to obtain eight input images to be processed.

The information processing apparatus 801 controls the illumination apparatuses 805 to 812 in the above-described manner and performs the information processing for detecting the anomaly by using the plural types of video pictures which are shot and transmitted by the image pickup apparatus 803.

The inspection target object 802 is an object set as a target to be determined as normal or abnormal by the information processing apparatus 801.

A display apparatus 804 is constituted by a monitor or the like. A determination result display example to the display apparatus 804 is similar to that of the first embodiment as illustrated in FIG. 2.

Figure 9:
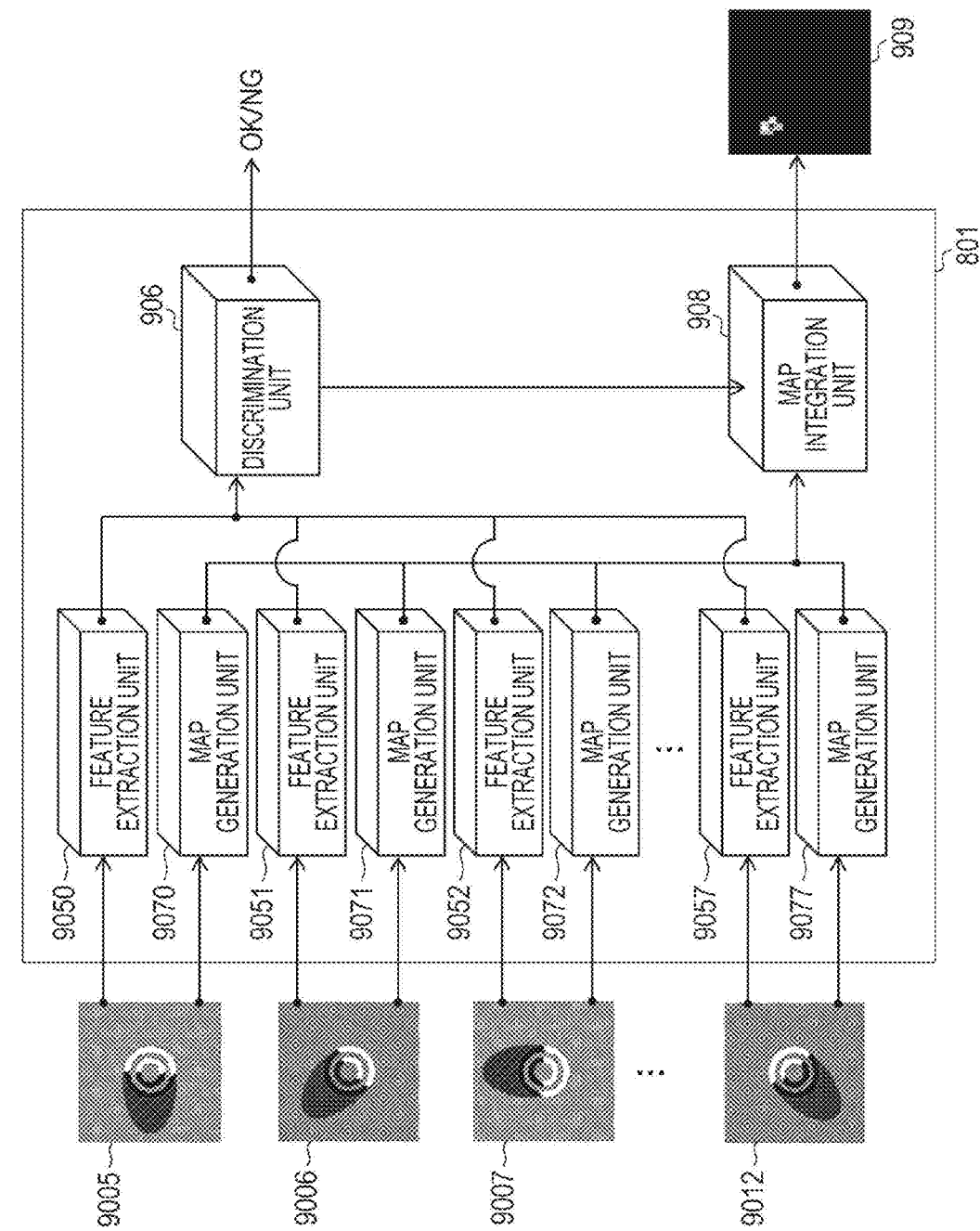
FIG. 9 is a functional block diagram of the information processing apparatus according to the second embodiment.

FIG. 9 is a functional block diagram of the present embodiment. Hereinafter, respective functions of the information processing apparatus in FIG. 9 according to the present embodiment will be described.

Input images 9005 to 9012 are images in which the inspection target object is shot by the image pickup unit 803 under the illumination environment formed by the illumination apparatuses 805 to 812. Feature extraction units 9050 to 9057 respectively extract feature amounts from the input images 9005 to 9012. According to the present embodiment, similarly as in the first embodiment, the maximum value, the average value, the variance, the kurtosis, the skewness, the contrast, the maximum gradient, or the like is extracted from the image obtained by performing the frequency conversion on the input image as the feature amount.

A discrimination unit 906 determines whether the inspection target object included in the input images 9005 to 9012 is normal or abnormal by using the feature amounts extracted by the feature extraction units 9050 to 9057.

Map generation units 9070 to 9077 generate respectively corresponding maps of the respective feature amounts corresponding to the extracted features from the input images 9005 to 9012.

Figure 10:
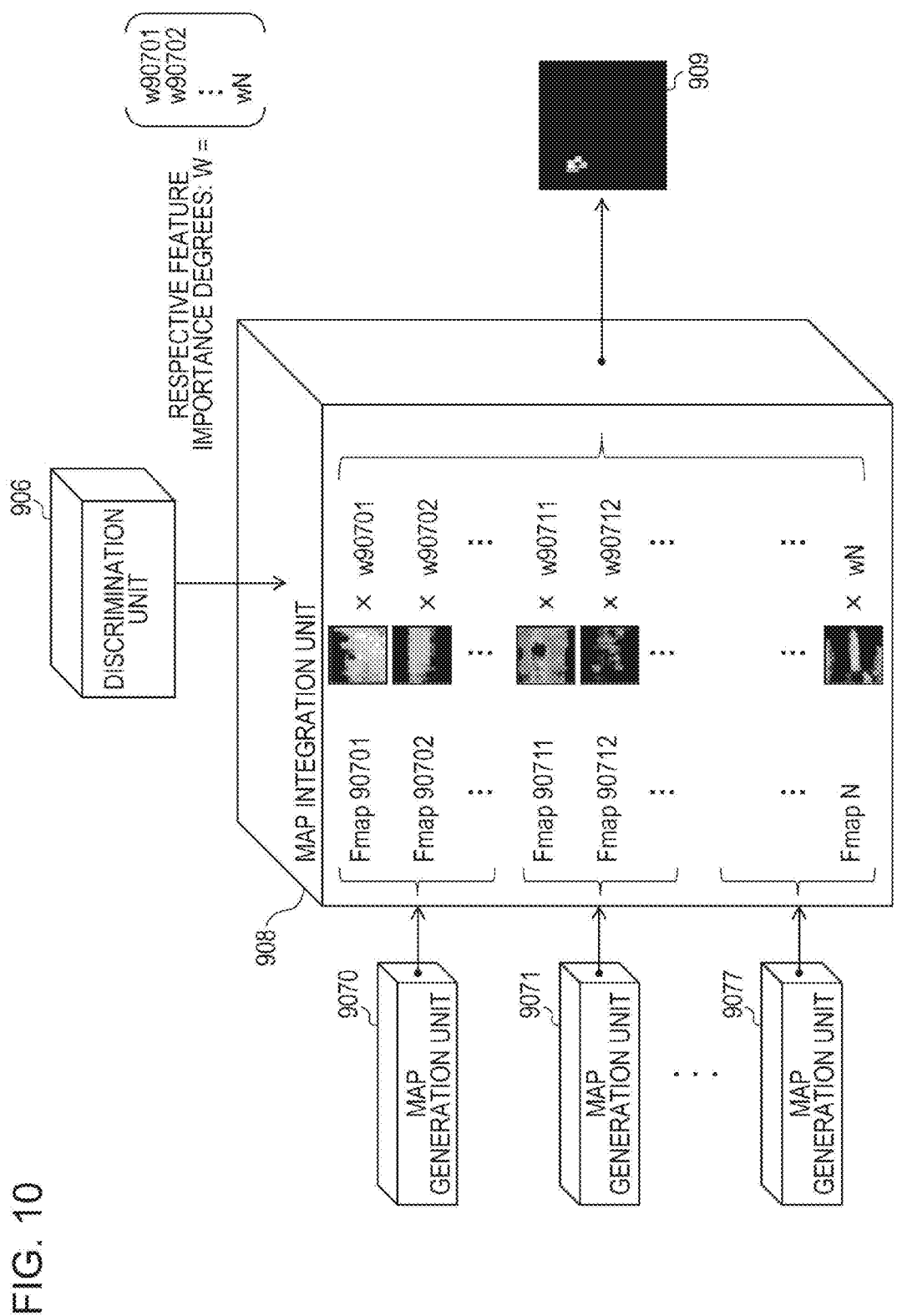
FIG. 10 is a block diagram illustrating a detail of the processing content of the map integration unit of FIG. 9 according to the second embodiment.

A map integration unit 908 refers to contribution degrees of the respective feature amounts with respect to the discrimination result obtained at the time of the discrimination by the discrimination unit 906 and integrates the plurality of maps generated for each of the feature amount by the map generation units 9070 to 9077 to generate a visualized image 909 in which the defect candidate area is visualized. The processing for generating the visualized image 909 is similarly performed as in the first embodiment, but a difference resides in the number of input images. According to the first embodiment, the inspection is performed by using the feature amount group extracted from the single input image, but according to the present embodiment, the inspection is performed by using the feature amount group extracted from the plurality of images similarly like the feature amount group extracted from the single input image according to the first embodiment. Here, a method of generating a visualized image will be described with reference to a concept diagram of FIG. 10. The concept diagram of FIG. 10 represents a detail of the map integration unit 908 of FIG. 9.

Hereinafter, the processing flow chart according to the present embodiment will be described with reference to FIG. 3.

(Step S301)

The series of processings such as the feature extraction in step S301 are similar to those of the first embodiment. Feature amounts are respectively extracted from the input images 9005 to 9012 by the respectively corresponding feature extraction units 9050 to 9057. According to the method for the feature extraction from the single input image, a plurality of hierarchical images are generated through the image decomposition from the high frequency components into images of frequency components in the vertical, horizontal, and diagonal directions of the low frequency components by the filter processing based on the Haar Wavelet conversion. Thereafter, a plurality of feature amounts are extracted from the plurality of generated hierarchical images. With regard to the feature amounts extracted herein too, similarly as in the first embodiment, the feature amount with which the abnormal data can be highly accurately detected is selected in advance. It should be however noted that, according to the present embodiment, since the feature extraction processing before the feature selection is performed on all of the eight input images, the extracted feature amount is selected in a state in which the 8-fold feature amounts are extracted as compared with the first embodiment. Thereafter, a satisfactory combination of the feature amounts is searched for from among all of these extracted features. The selection may be carried out by using LASSO, graph cut, the feature selection technique using the genetic algorithm, and the like in the related art as the feature selection method. As a result of the feature selection, the feature amounts extracted by the feature extraction units 9050 to 9057 do not necessarily need to respectively have the same feature amount set, and also the numbers of extracted feature amounts do not necessarily need to equal to one another. In some cases, the number of features extracted from the image shot under certain illumination conditions may be 0.

Hereinafter, with regard to the feature amounts eventually selected by the feature selection processing in advance, the total number of the feature amounts extracted from all the input images is set as several tens of feature amounts.

(Step S302)

In step S302, the feature amounts extracted in step S301 are transmitted from the feature extraction units 9050 to 9057, and the normal/abnormal determination is performed by the discrimination unit 906. It should be noted that, according to the present embodiment, the discrimination unit 906 determines whether an anomaly exists on the basis of a distance from a higher dimension surface representing a normal area that has been learnt as a normal distribution by the subspace method similarly as in the first embodiment. The calculation method for the contribution degrees of the respective feature amounts with respect to the anomaly score is executed similarly as in the first embodiment, and the calculated contribution degrees of the respective feature amounts are output. In step S303, the discrimination unit determines whether it is normal or abnormal.

(Step S304)

In step S304, it is determined as to whether or not the defect candidate area visualization based on the anomaly score maps is performed. The user may previously set whether or not the defect candidate area visualization is performed. When it is set that the anomaly score map visualization is not performed, the processing proceeds to step S305. When it is set that the anomaly score map visualization is performed, the processing proceeds to step S306 to perform the defect candidate area visualization. Whether the processing proceeds to step S306 or step S305 may be determined on the basis of the determination result as normal or abnormal obtained in step S304. That is, when it is determined as abnormal, the processing may automatically proceed to step S306.

(Step S305)

In step S305, the map integration unit 908 outputs information as to whether it is normal or abnormal, the anomaly score, and the like to the display apparatus 104.

(Step S306)

In step S306, the defect area is visualized. This processing will be described by using the processing flow chart of FIG. 4.

(Step S308)

In step S308, the map generation units 9070 to 9077 obtain the input images 9005 to 9012.

(Step S309)

In step S309, the map generation units 9070 to 9077 calculate score maps representing the scores of the feature amounts extracted in step S301 similarly as in the first embodiment.

(Step S310)

In step S310, the map generation units 9070 to 9077 perform the normalization of the score maps obtained in step S309 similarly as in the first embodiment.

(Step S311)

In step S311, the map integration unit 908 determines whether only values of the score maps higher than or equal to the threshold are left or all the values are left on the basis of the user setting. If the threshold cutoff is set, all the areas lower than or equal to the threshold are set as 0 in step S313.

(Step S312)

In step S312, the map integration unit 908 reads the contribution degrees of the feature amounts output in step S302 and integrates the respective score maps to one another by using the contribution degrees as the importance degrees of the respective score maps to create the defect display image. The process of creating the image on which the importance degrees are affected at this time will be illustrated in the conceptual diagram of FIG. 10. The conceptual diagram of FIG. 10 represents a detail of the map integration unit 908 of FIG. 9. In the map integration at this time too, the plurality of input images are used. Maps Fmap90701 to FmapN respectively calculated from the feature amounts are multiplied by corresponding importance degrees, and a linear sum is calculated for each of the same pixels in all the maps to generate a single defect display image. It should be noted that, when the respective score maps are integrated to one another, the respective score maps are once converted to have the same resolution as the original input images 9005 to 9012 and then integrated to one another. If the image sizes of the input images 9005 to 9012 are different from each other, those image sizes are converted into the same size (for example, to be matched with the largest size of the input image) and coupled to one another.

The defect display image is an image in which the defect area is emphasized and an image indicating a reason why it is determined as abnormal by the discrimination unit 406.

(Step S313)

In step S313, the map integration unit 908 sets all scores of the areas having the scores lower than or equal to the threshold as 0 in the respective maps normalized in step S310. Accordingly, since only the defect area has a score, in a case where the defect area is superposed on the input image 401 to be displayed, it is facilitated for the user to recognize the location of the defect area.

(Step S307)

In step S307, the map integration unit 908 outputs the score maps generated in step S306 to the display apparatus 104 to be displayed. In step S305, the map integration unit 408 outputs the information as to whether it is normal or abnormal, the anomaly score, and the like, and the processing is ended.

According to the present embodiment, the user can intuitively find out the reason why the inspection target is determined as abnormal together with the result of the abnormal determination. For this reason, the above-described configuration is beneficial when the parameter related to the inspection is adjusted and when the number of occurrences of the particular abnormal patterns is found out to provide the feedback to the process in the production line as the countermeasure to carry out the modification. In addition to the above, it is possible to find out an important shooting condition depending on the shot images obtained under the plurality of illumination conditions and the contribution degrees of the feature amounts output in S302 corresponding to the respective images, and a tendency that the defect is more likely to be recognized under which shooting condition.

Third Embodiment

Hereinafter, a third embodiment (exemplary embodiment) of the present invention will be described with respect to the drawings. Similarly as in the second embodiment, according to a method of the third embodiment, a plurality of images are obtained by shooting the single inspection target. For the image indicating the reason of the inspection result in a case where the feature amount of each of the images is extracted to perform the appearance inspection, a synthesis image in which an anomaly area is emphasized and shot from the input image shot under a plurality of illumination conditions is displayed as the visualization result instead of the visualized image based on the anomaly score maps. According to the present embodiment, for example, in an initial setting, even when the inspection is carried out by performing the shooting without adjusting illumination conditions like the illumination apparatuses 805 to 812 as illustrated in FIG. 8, images can be synthesized to one another to obtain a synthesis image as a defect area emphasis image obtained by an optimal combination of the illumination conditions such that it is easy for the user to intuitionally recognize, and the synthesis image can be presented to the user.

Figure 11:
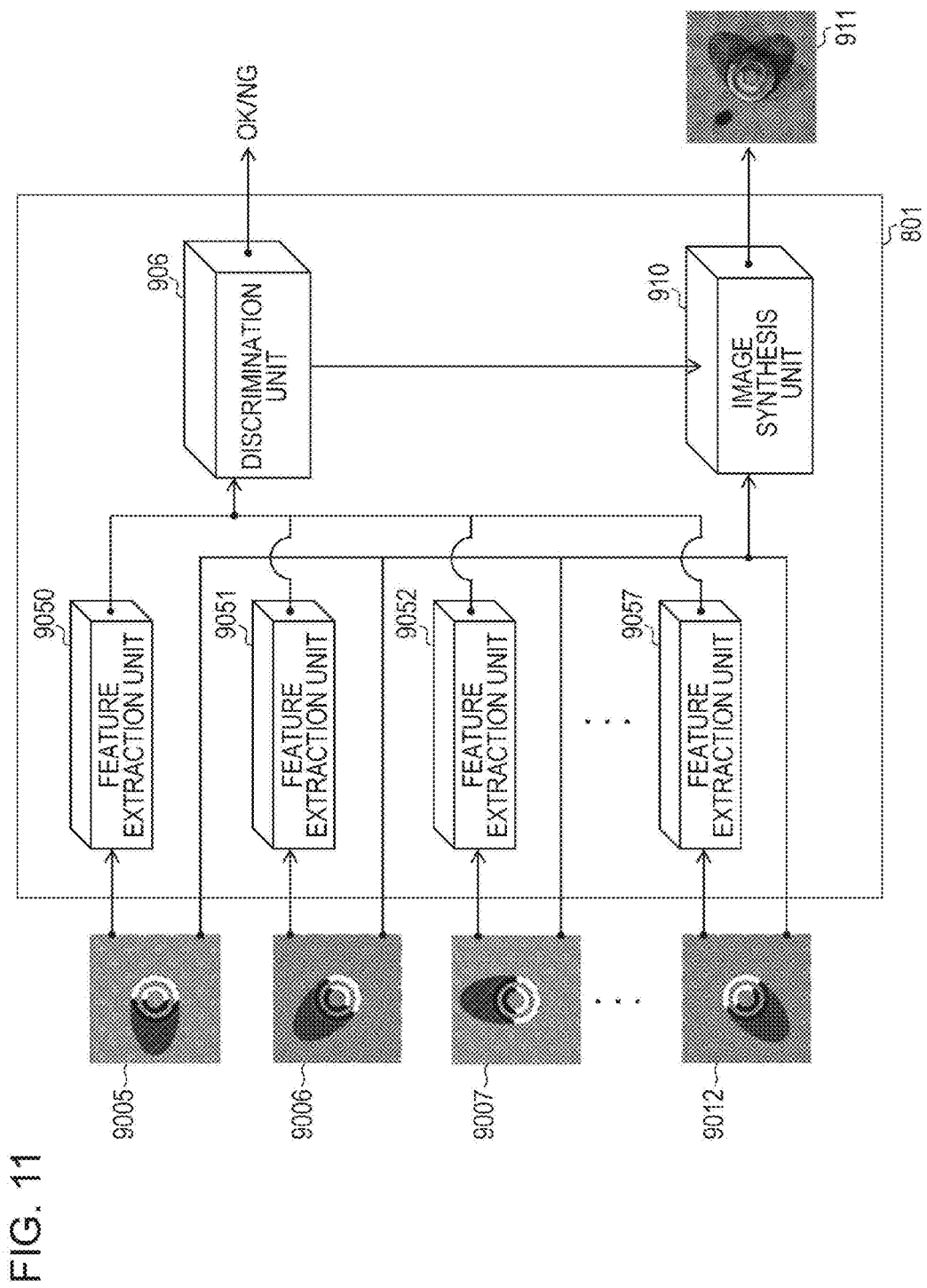
FIG. 11 is a functional block diagram of the information processing apparatus according to the third embodiment.
Figure 15:
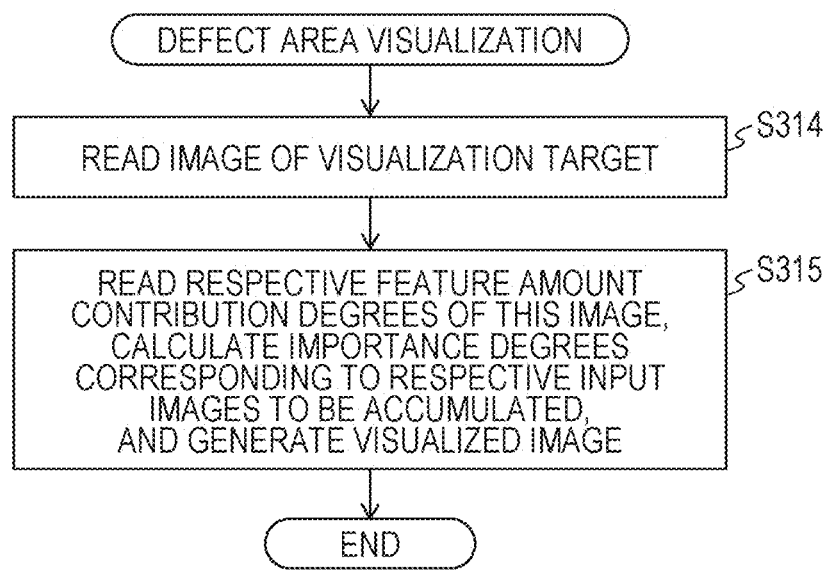
FIG. 15 is a processing flow chart according to the third embodiment.

A difference between the present embodiment and the second embodiment will be described by way of comparison between FIG. 9 and FIG. 11. According to the present embodiment, the map generation units 9070 to 9077 and the map integration unit 908 according to the second embodiment do not exist, and an image synthesis unit 910 that receives an input image and outputs a visualized image 911 exists instead. Thus, the process flow related to S301 to S307 illustrated in FIG. 3 are similar to that of the second embodiment except that the flow for the visualization of the defect area in S306 is replaced by FIG. 15 according to the present embodiment.

Step S314

In step S314, the input images 9005 to 9012 are read to be transmitted to the image synthesis unit 910.

Step S315

Figure 12:
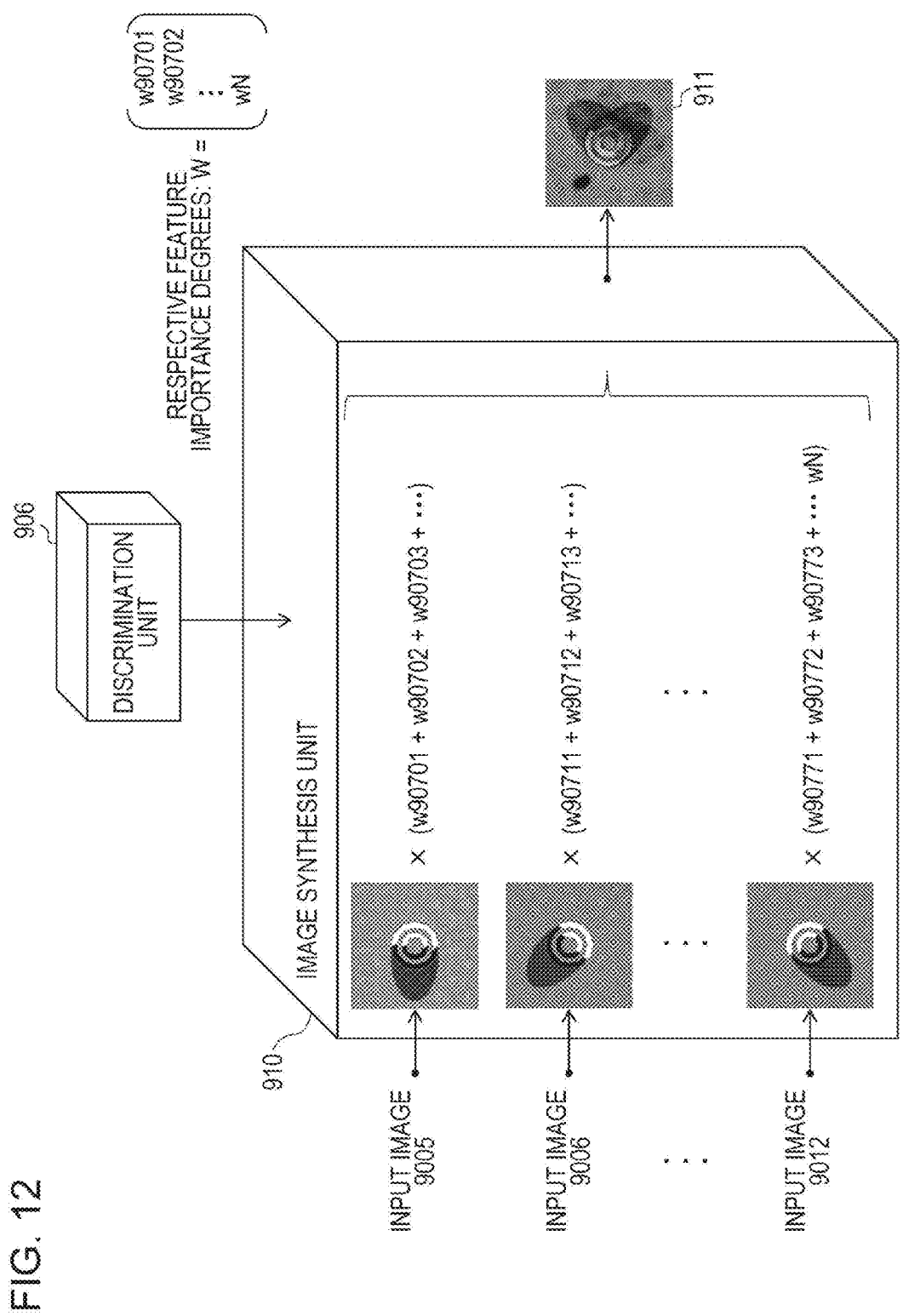
FIG. 12 is a block diagram illustrating a detail of a processing content of an image synthesis unit of FIG. 11 according to the third embodiment.

The contribution degrees (importance degrees) of the respective feature amounts output in step S302 are transmitted from the discrimination unit 906 to the image synthesis unit 910. Thereafter, the importance degrees corresponding to the respective input images are calculated. FIG. 12 illustrates a detail an example of the processing by the image synthesis unit 910. The importance degrees corresponding to the respective input images 9005 to 9012 are defined by a sum of the importance degrees corresponding to the respective input images among the respective feature amount importance degrees. A value obtained by integrating the importance degrees calculated with respect to the respective input images may take a decimal format, and takes a two-dimensional matrix formation exceeding a luminance range of 0 to 255. These obtained results are accumulated, and the eventually obtained two-dimensional matrix is normalized again to be contained in the range of 0 to 255 to obtain the visualized image 911.

Fourth Embodiment

Hereinafter, a fourth embodiment (exemplary embodiment) of the present invention will be described with respect to the drawings. According to the fourth embodiment, in a case where a plurality of images are obtained by shooting the single inspection target and the appearance inspection is performed by extracting feature amounts from the images, an anomaly degree for each of the images is calculated by a discriminator, and the anomaly degrees by the number of the input images are integrated to one another to determine again whether it is normal or abnormal, and also an image indicating a reason of the inspection result is generated by setting a plurality of anomaly scores at this time as a reference.

According to the second embodiment, when the shot images obtained under the plurality of illumination conditions are input, the feature amounts extracted from the picked-up images are integrated to one another to be determined as normal or abnormal by the single discriminator. However, since it takes time to perform the individual shooting in actual use cases in the production line, in particular, if the inspection is not performed until all the shootings are ended, this may be inconvenient in terms of takt time. In view of the above, in a case where the above-described inspection is performed, a line is designed in which inspection apparatuses that detect anomalies having different tendencies for the respective input images are arranged. In the above-described case too, it is aimed at generating an image indicating a reason of an inspection result by using the anomaly score output by each discriminator.

Figure 13:
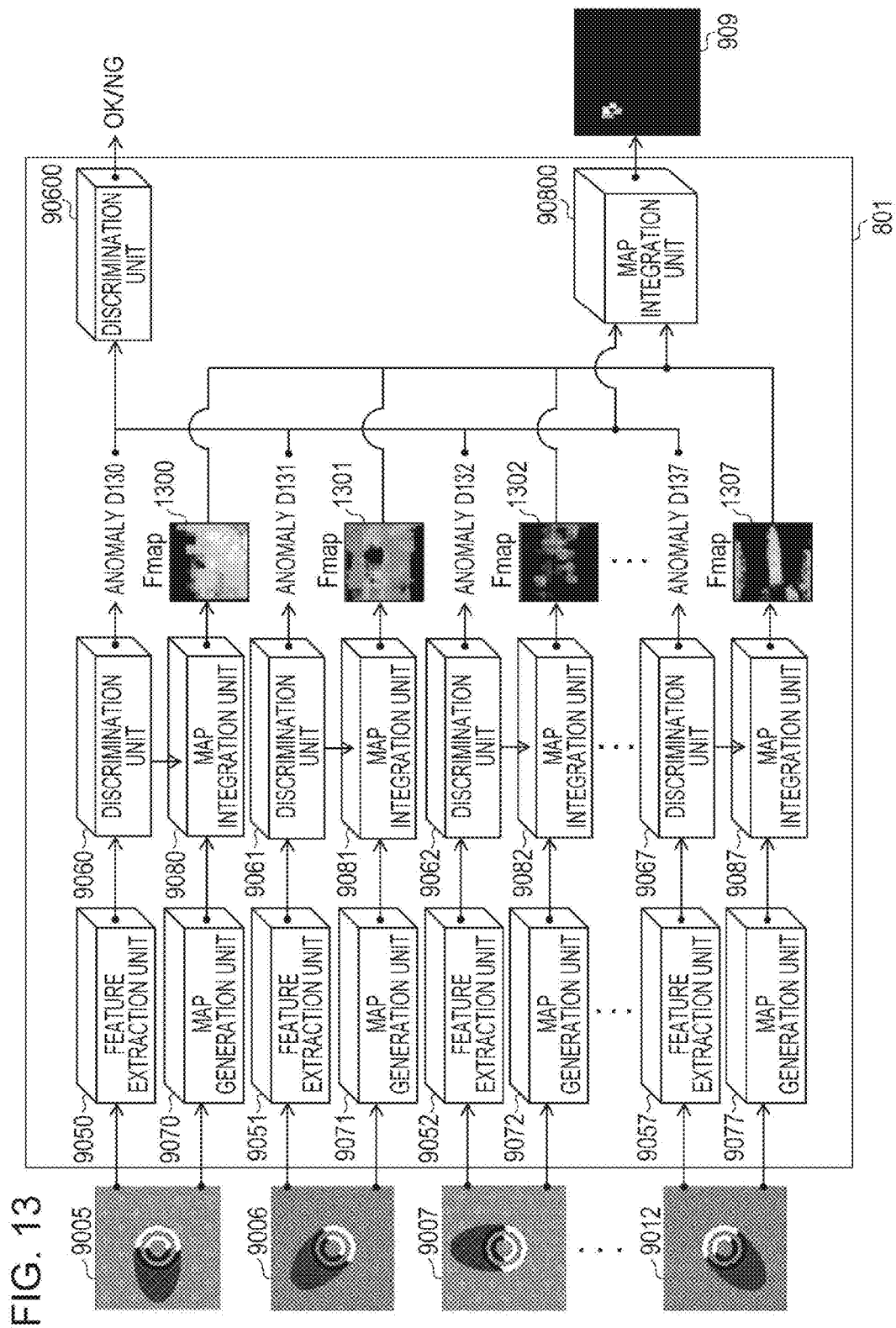
FIG. 13 is a functional block diagram of the information processing apparatus according to the fourth embodiment.
Figure 14:
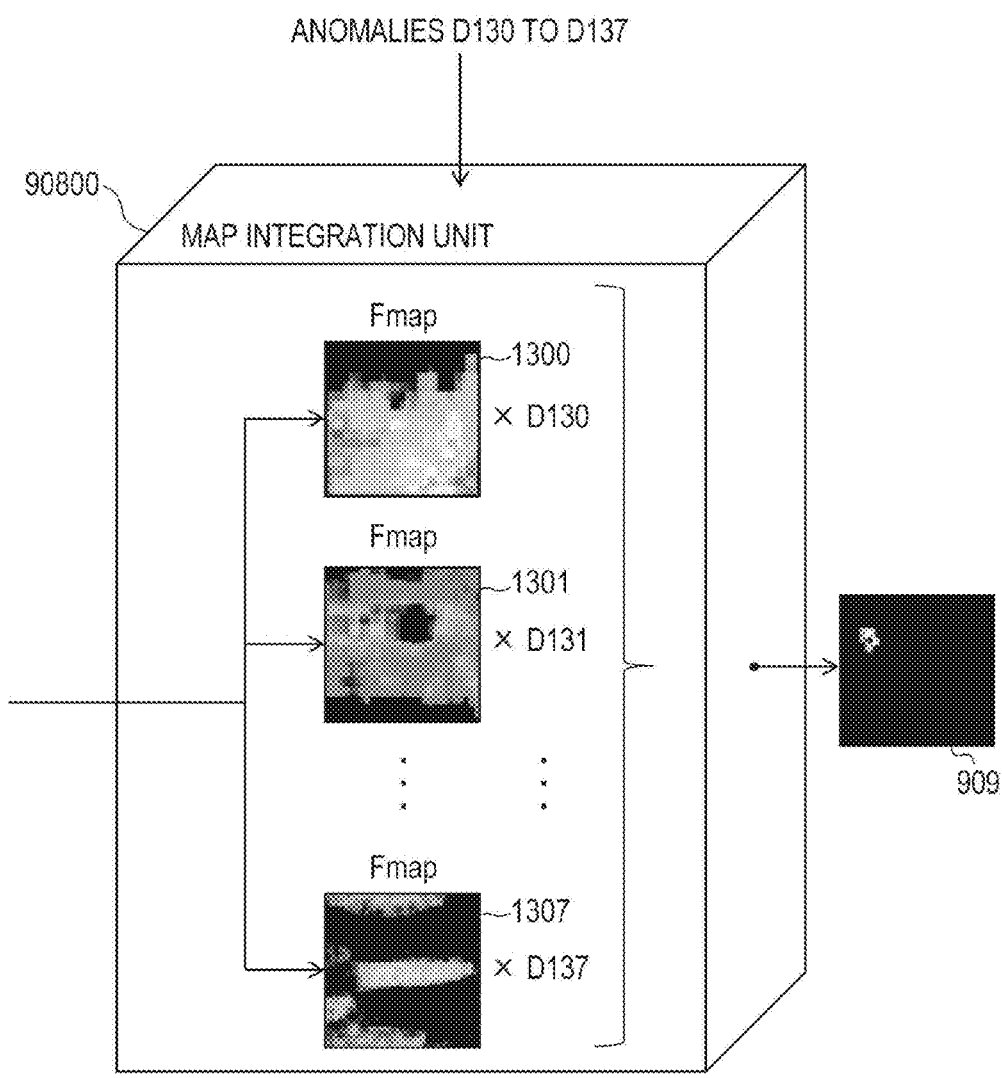
FIG. 14 is a block diagram illustrating a detail of the processing content of the map integration unit of FIG. 13 according to the fourth embodiment.

In FIG. 13, the input images 9005 to 9012 are input, and the feature amounts previously selected in the feature extraction units 9050 to 9057 from the input images 9005 to 9012 are extracted. Anomaly degrees D130 to D137 are calculated for the respectively extracted feature amounts in discrimination units 9060 to 9067. Herein, the discrimination units 9060 to 9067 perform discrimination, for example, by the subspace method or the like, and uses a method with which it is possible to calculate a distance from a distribution of normal data as the anomaly degree. Each discrimination processing and processing of outputting the map by map integration units 9080 to 9087 are similar to those according to the first embodiment where one input image is shot, and the discrimination processing and the visualized image generation are performed. The anomaly degrees by the number of input images are further transmitted to a discrimination unit 90600 to determine a result in a comprehensive manner so that it is determined whether the inspection target is normal or abnormal. The discrimination unit 90600 may use any discrimination method. For example, a simple method may be used such as a method of performing a threshold determination on a total value of the anomaly degrees D130 to D137 or a method of previously setting a threshold for each of the anomaly degrees D130 to D137 and determining as abnormal in a case where even one of the anomaly degrees exceeds the threshold. Thereafter, feature amount maps Fmap1300 to Fmap1307 calculated by the respective map integration units 9080 to 9087 are transmitted to a map integration unit 90800. Then, the map integration unit 90800 receives the anomaly degrees D130 to D137 output by the discrimination units 9060 to 9067. As illustrated in FIG. 14, the corresponding anomaly degrees with respect to the respective feature amount score maps are integrated and accumulated to one another to generate the visualized image 909. This is based on an idea that, since it is conceivable that the objects having high anomaly degrees strongly reflects the respective anomaly tendencies, this can be treated equivalently with the importance degree according to the first to third embodiments.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-251881, filed Dec. 12, 2014, and Japanese Patent Application No. 2015-187463, filed Sep. 24, 2015, which are hereby incorporated by reference herein in their entirety.

The invention claimed is:

1. An information processing apparatus comprising:
one or more processors; and
a memory coupled to the one or more processors, the memory having stored thereon instructions which, when executed by the one or more processors, cause the information processing apparatus to perform operations including:

extracting a plurality of types of feature amounts from an image including an inspection target object, determining an anomaly degree of the inspection target object based on the extracted plurality of types of feature amounts, generating a plurality of feature amount maps each for representing a distribution of feature amounts of respective one of the extracted plurality of types of feature amounts, integrating the generated plurality of feature amount maps to obtain an integrated map based on contribution degrees of the respective plurality of feature amounts with respect to the determined anomaly degree, and displaying, on a display, the integrated map as a defect image representing a defect included in the inspection target object.

2. The information processing apparatus according to claim 1, wherein executing the instructions further causes the information processing apparatus to perform operations including generating plural pieces of score information, each representing a score of each of the plurality of feature amounts from the image, wherein the anomaly degree is determined based on the plural pieces of score information.

3. The information processing apparatus according to claim 2, wherein the score information is two-dimensional array information having a number of dimensions that is the same as a number of dimensions of the image.

4. An information processing apparatus comprising:

one or more processors; and a memory coupled to the one or more processors, the memory having stored thereon instructions which, when executed by the one or more processors, cause the information processing apparatus to perform operations including:

extracting a plurality of feature amounts from a plurality of images including an inspection target object, determining an anomaly degree of the inspection target object based on the extracted plurality of feature amounts, generating an image in which a defect included in the inspection target object is emphasized, by synthesizing the plurality of images to one another based on contribution degrees of the respective plurality of feature amounts with respect to the determined anomaly degree, and displaying, on a display, the generated image in which the defect included in the inspection target object is emphasized.

5. The information processing apparatus according to claim 4, wherein the plurality of images are images including the inspection target object which are respectively irradiated with different pattern illuminations.

6. The information processing apparatus according to claim 1, wherein executing the instructions further causes the information processing apparatus to perform operations including determining whether the inspection target object is normal or abnormal based on the anomaly degree.

7. The information processing apparatus according to claim 1, wherein executing the instructions further causes the information processing apparatus to perform operations including generating a plurality of hierarchical images having different resolutions by performing a predetermined conversion on the image, and wherein extracting includes extracting the plurality of feature amounts from the plurality of hierarchical images.

8. The information processing apparatus according to claim 7, wherein the plurality of feature amounts include at least one of the following: a maximum value, an average value, a variance, a kurtosis, a skewness, a contrast, and a maximum gradient of pixel values in the plurality of hierarchical images.

9. The information processing apparatus according to claim 7, wherein the predetermined conversion includes Wavelet conversion.

10. A method for an information processing apparatus the method comprising:

extracting a plurality of types of feature amounts from an image including an inspection target object;

determining an anomaly degree of the inspection target object based on the extracted plurality of types of feature amounts;

generating a plurality of feature amount maps each for representing a distribution of feature amounts of respective one of the extracted plurality of types of feature amounts;

integrating the generated plurality of feature amount maps to obtain an integrated map based on contribution degrees of the respective plurality of feature amounts with respect to the determined anomaly degree; and displaying, on a display, the integrated map as a defect image representing a defect included in the inspection target object.

11. A method for an information processing apparatus the method comprising:

extracting a plurality of feature amounts from a plurality of images including an inspection target object;

determining an anomaly degree of the inspection target object based on the extracted plurality of feature amounts;

generating an image in which a defect included in the inspection target object is emphasized, by synthesizing the plurality of images to one another based on contribution degrees of the respective plurality of feature amounts with respect to the determined anomaly degree; and displaying, on a display, the generated image in which the defect included in the inspection target object is emphasized.

12. A non-transitory computer readable storage medium storing a program causing a computer to execute the method according to claim 10.

13. A non-transitory computer readable storage medium storing a program causing a computer to execute the method according to claim 11.

* * * * *